US007410259B2

(12) United States Patent
Kurtzberg et al.

(10) Patent No.: US 7,410,259 B2
(45) Date of Patent: Aug. 12, 2008

(54) OPTIMAL DYNAMIC TECHNIQUES FOR CUSTOM-FIT EYE OPTICS

(75) Inventors: Jerome M. Kurtzberg, Yorktown Heights, NY (US); Menachem Levanoni, Poway, CA (US)

(73) Assignee: International Business Machines Corporation, Armonk, NY (US)

( * ) Notice: Subject to any disclaimer, the term of this patent is extended or adjusted under 35 U.S.C. 154(b) by 309 days.

(21) Appl. No.: 11/380,503

(22) Filed: Apr. 27, 2006

(65) Prior Publication Data

US 2007/0252952 A1 Nov. 1, 2007

(51) Int. Cl.
*G01B 3/00* (2006.01)

(52) U.S. Cl. ...................................... 351/246; 351/206

(58) Field of Classification Search ................. 351/246, 351/247, 206, 205, 200; 702/84
See application file for complete search history.

(56) References Cited

U.S. PATENT DOCUMENTS 6,188,967 B1 * 2/2001 Kurtzberg et al. ............. 702/84

* cited by examiner

*Primary Examiner*—Hung X Dang
(74) *Attorney, Agent, or Firm*—McGinn IP Law Group, PLLC; Gail H. Zarick

(57) ABSTRACT

A computer method for providing optimal dynamic techniques for custom-fit eye optics. The method includes steps of mounting pressure and motion sensors in a eye-enclosing device, transmitting data produced by said sensors during actual operation of said eye-enclosing device worn by a specific individual, receiving said sensor signals for subsequent analysis by a computer, creating a stress-and-motion map based on said sensor-based data, and creating a virtual optic (model) for optimal support and comfort based on step iv stress-and-motion map.

1 Claim, 1 Drawing Sheet

OPTIMAL DYNAMIC TECHNIQUES FOR CUSTOM-FIT EYE OPTICS

BACKGROUND OF THE INVENTION

1. Field of the Invention

This invention relates to methodology for utilizing continual sensor-based data to design and adjust optics to fit an individual, in a given dynamic environment, in an optimal manner.

2. Introduction to the Invention

Static fitting techniques to design and construct optics for specific people are known. A vision test is taken and the optics is produced based on that test. However, no attention is given to the dynamic workings of the eye in the changing real environment. Specifically, the stresses and accelerations experienced by the eye during normal operation are not taken into account, nor is the optimum balance, between near and far vision, taken into account.

SUMMARY OF THE INVENTION

We have now discovered novel methodology for exploiting the advantages inherent generally in sensing the dynamic workings (stresses) on specific eyes in actual motion, and using the sensor-based data to optimize the design and construction of the desired optics.

Our work proceeds in the following way.

We have recognized that a typical and important paradigm for presently effecting optics construction, is a largely static and subjective, human paradigm, and therefore exposed to all the vagaries and deficiencies otherwise attendant on static and human procedures. Instead, the novel paradigm we have in mind works in the following way:

First, a patient wears a set of pressure and movement sensors mounted, say, inside a eye-encasing device (glasses). These sensors record their associated stesses and eye-movement produced in normal individual motion in its dynamic environment for a prescribed period of time sufficient to capture all possible stress and eye-movement patterns.

The dynamically acquired data are fed into a computer which creates a map of the forces and eye-motion experienced by the examined eye. This information is used to design an optimal optic which maximizes vision and minimizes discomfort, and results in a computer production of a virtual optics that offers optimal performance to the examined eye in its normal operation.

A physical optic is then produced from a model provided by the virtual optic. This physical optic provides maximum vision and maximal comfort to its wearer, following the optimal design of the optic.

We now itemize a novel computer method which can preserve the advantages inherent in the static approach, while minimizing the incompleteness and attendant static nature and subjectivities that otherwise inure in a technique heretofore used.

To this end, in a list aspect of the present invention, we disclose a novel computer method comprising the steps of:

i) mounting pressure and motion sensors in an eye-enclosing device;

ii) transmitting data produced by said sensors during actual operation of said eye-enclosing device worn by a specific individual;

iii) receiving said sensor signals for subsequent analysis by a computer;

iv) creating a stress-and-motion map based on said sensor-based data; and v) creating a virtual optic (model) for optimal support and comfort based on step iv stress-and-motion map.

The novel method preferably comprises further step of actually constructing said physical optic.

BRIEF DESCRIPTION OF THE DRAWING

The invention is illustrated in the accompanying drawing, in which.

DETAILED DESCRIPTION OF THE PRESENT INVENTION

Typical Application

Figure 1:
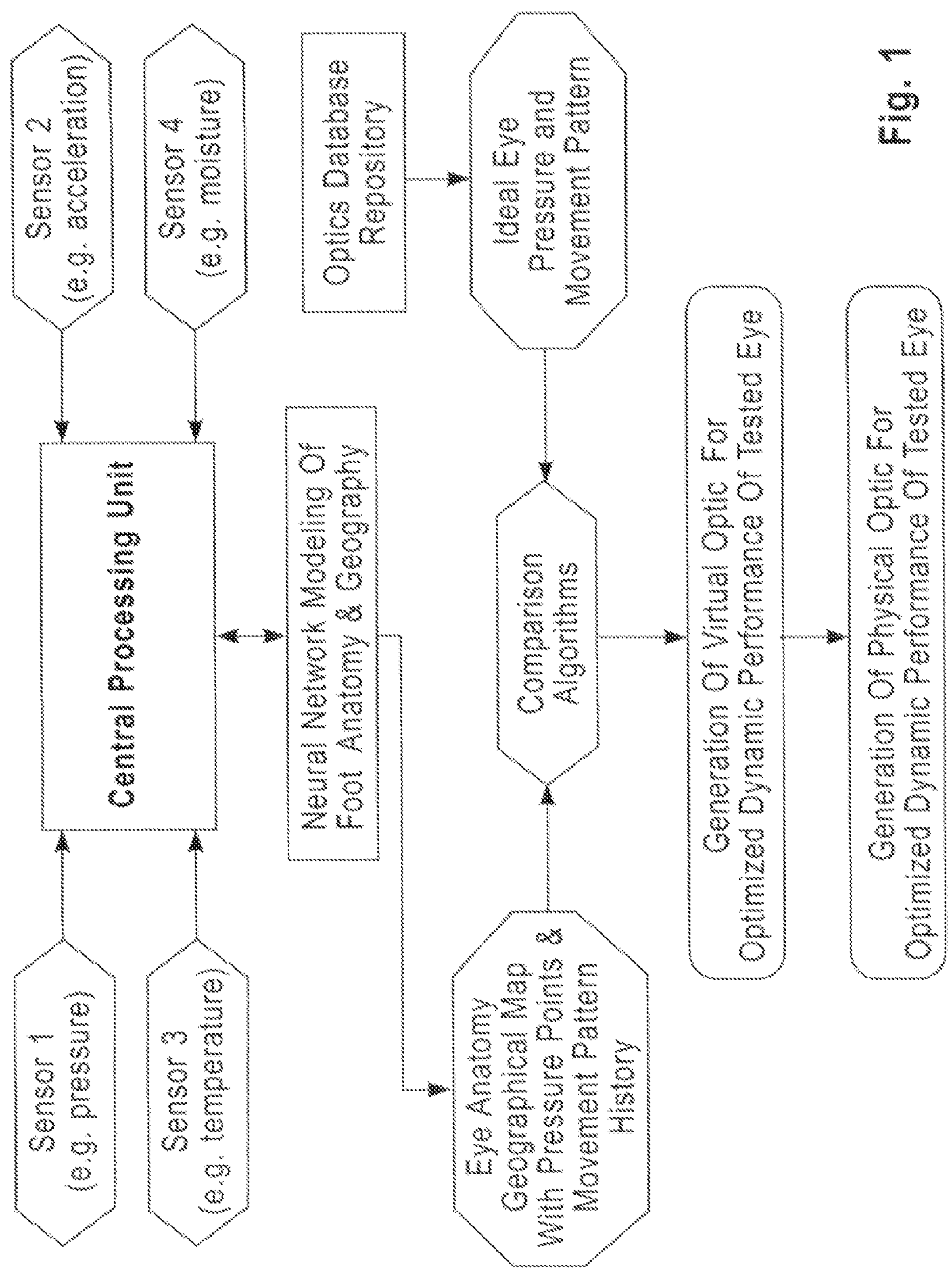
FIG. 1 (numerals 10-34) provides an illustrative flowchart comprehending overall realization of the method of the present invention, including details of individual components.

In a typical case (and with reference to FIG. 1), the patient's eye is fitted with a temporary device containing a number of sensors, located at prescribed locations on the tested eye. These sensors, which include pressure, motion, temperature, and humidity, are connected to a recording device.

The patient is asked to wear the device for several days and follow his/her normal routine.

During the test period, sensors data are recorded (including time stamps) in the recording device. The patient returns the device and the recording device at the end of the test period. The information stored in the recording device is then downloaded to a computer which stores all data in a database.

The data are then analyzed by a program (preferably a neural network modeling program) which creates maps of the tested eye at different times. These maps also contains the sensors' reading at these times. Thus the system now has information on the dynamic behavior of the tested eye, including parametric information.

Based on these maps and maps of an ideal eye under similar conditions, an optimization program designs an optimized virtual optic for the patient. This design is then fed to a machine which generates an optimized physical optic.

What is claimed:

1. A method of providing a custom eye optics, comprising:

mounting pressure and motion sensors in an eye-enclosing device;

transmitting data produced by said sensors during actual operation of said eye-enclosing device worn by a specific individual;

receiving said sensor signals for subsequent analysis by a computer;

creating a stress-and-motion map based on said sensor-based data;

creating a virtual optic for optimal support and comfort based on the created stress-and-motion map;

correlating a temperature sensor with vision and comfort of a worn optic;

interpolating map stresses and motions experienced by an eye over a period of time;

updating the virtual optic model using the interpolating map; and designing the visual optic according to the interpolated map.

* * * * *